United States Patent [19]

Yeh et al.

[11] Patent Number: 4,528,401

[45] Date of Patent: Jul. 9, 1985

[54] CATALYTIC PROCESS FOR THE MANUFACTURE OF KETONES

[75] Inventors: Chuen Y. Yeh, Edison; Charles Savini, Warren, both of N.J.

[73] Assignee: Exxon Research & Engineering Co., Florham Park, N.J.

[21] Appl. No.: 516,903

[22] Filed: Jul. 25, 1983

Related U.S. Application Data

[63] Continuation-in-part of Ser. No. 420,715, Sep. 21, 1982, abandoned, and Ser. No. 420,627, Sep. 21, 1982, abandoned.

[51] Int. Cl.$^3$ ............................................. C07C 45/42
[52] U.S. Cl. .................................. 568/408; 568/400; 568/365; 568/360; 568/69; 568/896; 568/899
[58] Field of Search ............... 568/408, 400, 401, 365, 568/360

[56] References Cited

U.S. PATENT DOCUMENTS

| | | | |
|---|---|---|---|
| 2,523,686 | 5/1947 | Engel | 260/597 |
| 2,635,119 | 4/1953 | Finch et al. | 260/597 |
| 3,129,253 | 4/1964 | Odioso et al. | 568/408 |
| 4,022,837 | 5/1977 | Schneider | 260/597 |
| 4,243,553 | 1/1981 | Naumann et al. | 252/439 |
| 4,243,554 | 1/1981 | Naumann et al. | 252/439 |

FOREIGN PATENT DOCUMENTS

| | | |
|---|---|---|
| 59179 | 3/1947 | Netherlands . |
| 876024 | 1/1958 | United Kingdom . |
| 1029175 | 5/1963 | United Kingdom . |
| 1436887 | 7/1973 | United Kingdom . |
| 1495011 | 2/1974 | United Kingdom . |

OTHER PUBLICATIONS

*Angew. Chem. Int. Ed. Engl.*, 17, 535 (1978).
Muller et al., *Angew. Chem. Int. Ed. Engl.*, 17, 279 (1978).
*J. Inorg. Nucl. Chemistry*, 35, 1895–1904 (1973).

*Primary Examiner*—James H. Reamer
*Attorney, Agent, or Firm*—Jack B. Murray, Jr.

[57] ABSTRACT

An improved process is provided for forming ketones from the corresponding olefins in the vapor phase in the presence of water vapor employing a heterogeneous catalyst comprising a molybdenum disulfide catalyst formed by the thermal decomposition of a thiomolybdate compound. It has been surprisingly found that these catalysts effect the formation of ketones in high selectivities with minimal selectivities to the undesirable carbon dioxide and carbon monoxide by-products.

20 Claims, No Drawings

CATALYTIC PROCESS FOR THE MANUFACTURE OF KETONES

CROSS-REFERENCE TO RELATED APPLICATIONS

This application is a continuation-in-part of our copending applications Ser. Nos. 420,715 and 420,627, both filed on Sept. 21, 1982 both now abandoned, and is related to our applications filed on even date herewith, Ser. No. 516,537 filed 7/25/1983 entitled "Catalytic Process for the Manufacture of Ketones", which is a continuation-in-part of Ser. Nos. 420,525; 420,526; 420,648 and 420,716, all filed on Sept. 21, 1982 all now abandoned; Ser. No. 516,902 7/25/1983 entitled "Improved Catalysts and Process for the Conversion of Olefins to Ketones", which is a continuation-in-part of Ser. No. 516,901 7/25/1983, entitled "Improved Catalysts and Process for Conversion of Olefins to Ketones", which is a continuation-in-part of Ser. No. 420,626, filed on Sept. 21, 1982 now abandoned.

BACKGROUND OF THE INVENTION

1. Field of the Invention

This invention relates to process and catalyst useful in the manufacture of ketones from olefins, and more particularly to improved molybdenum sulfide catalysts useful in the vapor phase conversion of olefins to ketones.

2. Description of the Prior Art

U.S. Pat. No. 2,523,686 to W. F. Engel of Shell employs catalysts containing (1) an oxide of a metal of Groups II, III, IV or VI of the Periodic Table and (2) a metal or partially reduced oxide of a metal of Group IB, Group VII or Group VIII of the Periodic Table, and prepares saturated open-ended ketones from olefins of at least three carbon atoms per molecule in a vapor phase process in the presence of steam and under defined conditions. Dutch Pat. No. 59,179, also to W. F. Engel, relates to similar catalyst systems. The patent contains no working example to any Mo catalyst system.

U.S. Pat. No. 2,635,119 to Shell disclosed that ketones may be formed by contacting the selected olefin with a sulfide catalyst of Mo, W, Te or Se together with 0 to 40 mole percent of sulfides of Ni, Fe, or Co, in the presence of a large excess of water and at described reaction conditions. The patent contains only a single working example to a Mo sulfide ($MoS_3$) in a liquid phase reaction of 1-octene feed to a ketone.

British Pat. No. 876,024 converts olefins into the corresponding aldehydes and ketones by passing a mixture of the olefin and oxygen, optionally with steam, over catalysts containing metal compounds whose cations and metals of a transition metal of the fifth to eighth group or first sub-group of the Periodic System and whose anions are derived from strong acids. Exemplified strong acid salts are those containing halide (Cl, Br), $NO_3-$ and $PO_4=$.

British Pat. No. 1,436,887 to Shell relates to a process for forming ketones in which the selected alkene is contacted with water over certain catalysts in the presence of added $H_2S$ and in the substantial absence of $O_2$ in order to first form a secondary mercaptan which then reacts with the water to form the corresponding ketone. The catalysts comprise supported sulfide catalysts containing one or more metals of V, Nb, Ta, Cr, Mo, W and Mn, optionally with sulfides of Fe, Co, Ni, Ru, Rh, Pd, Os, Ir or Pt as promoter. The patent indicates that the selected support can be impregnated with a decomposable sulfur compound such as ammonium thiotungstate, and ammonium heptamolybdate is said to be a highly suitable water-soluble Mo compound. After drying and calcining, the dried, calcined solids are required to be sulfided, e.g., with $H_2S$, mercaptans, dialkyl disulfides, S or $CS_2$ in order to produce the catalyst.

British Pat. No. 1,495,011, also to Shell, relates to a process for forming a ketone from an alkene of 3 or more carbon atoms in which the alkene, water and $H_2S$ are contacted in the presence of certain supported sulfided trimetallic catalysts. The catalysts contain Mo, a Group VIII non-noble metal (Fe, Co and Ni) and a Group VIII noble metal and are prepared from the corresponding metal oxides (ammonium heptamolybdate is illustrated) followed by sulfiding of the oxide solids with a mixture of $H_2S$ and $H_2$.

U.S. Pat. No. 4,022,837 to Chevron relates to a process for producing a ketone by contacting water and the corresponding alkene with a catalyst consisting essentially of a hydrated molybdenum (VI)-oxygen compound such as molybdic oxide ($MoO_3$), molybdic acid, isomolybdic acid, the ammonium salts of these acids and hydrated modifications of the foregoing. During use of the catalyst, its activity for ketone formation declines, as the Mo(VI) atoms are reduced. Thereafter, the reduced Mo oxide is reoxidized to the +6 state by contacting the fixed catalyst bed with $O_2$.

British Pat. No. 1,029,175 describes a vapor phase process in which olefin is reacted with oxygen at temperatures of less than 350° C. in the presence of water vapor and a halogen, using a supported Group VIII noble metal catalyst containing either an iron, cobalt, nickel or Group I or VII transition metal compound optionally together with an alkali metal compound. Catalyst activity is stated to be further enhanced by additional use of one or more transition metal compounds of Groups III–VI, such as the rare earth metal compounds. The oxidation of propylene is indicated to give acetone as the main reaction product. Such a halide-containing catalyst system has severe disadvantages due to the corrosivity of halide-containing systems. In addition, the process of British Pat. No. 1,029,175 provides undesirably high selectivities to carbon dioxide by-product.

Thermal decomposition of various ammonium thiomolybdate salts is disclosed in U.S. Pat. Nos. 4,243,553 and 4,243,554 to Union Carbide to prepare catalysts for use in methanation and water gas shift reactions and in catalyzed hydrogenation, hydrodenitrogenation and hydrodesulfurization reactions. However, these patents do not relate to the use of the thus-prepared Mo catalysts in olefin oxidations.

SUMMARY OF THE INVENTION

An improved process is provided for forming ketones from the corresponding olefins in the vapor phase in a reaction zone in the presence of water vapor, and optionally in the additional presence of molecular oxygen employing a heterogeneous catalyst comprising molybdenum sulfide formed by thermal decomposition of certain ammonium thiomolybdate compounds. It has been surprisingly found that these catalysts effect the formation of ketones in very high selectivities with minimal selectivity loss to the undesirable carbon dioxide and carbon monoxide by-products, and without requiring the use of H₂S as a feed component, thereby avoiding the significant expense associated with the separation of unreacted H₂S from the product stream and the purification of the ketone to remove trace H₂S impurities.

It has been further found that the catalysts of this invention effect the above results without the formation of substantial amounts of hydrogenation by-products, such as butane from butene feeds, and such olefin saturation by-products have been detected in the gaseous effluents from the process of this invention in only minimal amounts, if at all.

In accordance with the preferred embodiment of the process of this invention, the ketone is formed in an $O_2$-free reaction zone, thereby avoiding the use of explosive $O_2$-olefin gas mixtures and greatly minimizing the hazards and expense associated with the handling of such $O_2$-olefin gas mixtures.

DETAILED DESCRIPTION OF THE INVENTION

Catalyst

The thermally decomposable thiomolybdate compounds which can be used in preparing the improved olefin oxidation catalysts of this invention are members selected from the group consisting of ammonium salts of molybdenum-sulfur cluster anions and compounds of the formula (I):

$$[R^1(R^2)N(R^3)R^4]_2MoO_xS_{4-x} \qquad (I)$$

wherein $R^1$, $R^2$, $R^3$ and $R^4$ can be the same or different and are hydrogen, alkyl, aryl, alkaryl, aralkyl, cycloalkyl, substituted derivatives of the above groups and mixtures thereof; and x is 0, 1 or 2. When any of $R^1$, $R^2$, $R^3$ and $R^4$ are alkyl, the alkyl group(s) can be branched or straight chain and will generally contain from 1 to 6 carbon atoms, and more preferably from 1 to 4 carbon atoms. Illustrative of such alkyl groups are methyl, ethyl, n-propyl, iso-propyl, n-, sec- and tert-butyl, and the like. When any of $R^1$, $R^2$, $R^3$ and $R^4$ are aryl, the aryl group will generally contain from 6 to 10 carbon atoms. Illustrative aryl groups are phenyl and naphthyl. When any of $R^1$, $R^2$, $R^3$, and $R^4$ are alkaryl, the alkaryl group will generally contain from 7 to 10 carbon atoms, preferably from 7 to 8 carbon atoms. Illustrative of such alkaryl groups are tolyl, xylyl, diethyl phenyl and the like. When $R^1$, $R^2$, $R^3$, and $R^4$ are aralkyl, the aralkyl group will generally contain from 7 to 10 carbon atoms, preferably from 7 to 8 carbon atoms. Illustrative of such aralkyl groups are benzyl, ethyl benzyl and the like. When any of $R^1$, $R^2$, $R^3$, and $R^4$ are cycloalkyl, the cycloalkyl group will generally contain from 3 to 8 carbon atoms, preferably from 5 to 6 carbon atoms. Illustrative of cycloalkyl groups are cyclopropyl, cyclobutyl, cyclohexyl, cyclooctyl, and the like. The foregoing groups can be unsubstituted or substituted by a substituent which does not interfere with the desired olefin oxidation. Illustrative of suitable substituents are hydroxy, halo, cyano, sulfo, alkoxy, aryloxy and the like.

As an example of an ammonium salt of a molybdenum-sulfur cluster anion for use in the practice of the invention is the crystalline compound $(NH_4)_2[Mo_3S(S_2)_6]x\ H_2O$ as disclosed in *Angew. Chem Int. Ed. Engl.* 17, 535 (1978) which also indicates that the existence of the homologous $(NH_4)_4[Mo_4S_4(S_2)_4]$ could be predicted. Another such cluster compound that can be used in the practice of the invention is $(NH_4)_2[Mo_2(S_2)_6]$ reported by Muller, et al., *Angew. Chem. Int. Ed. Engl.* 17, 279 (1978).

Illustrative examples of the thiomolybdate compounds of formula (I) are ammonium thiomolybdate [$(NH_4)_2MoS_4$], ammonium oxy thiomolybdate [$(NH_4)_2MoOS_3$], and bis (substituted aliphatic ammonium) thiomolybdate compounds of formula (I) are illustrated by those in which the ammonium moiety contains one alkyl group, such as $n\text{-}C_4H_9NH_3^+$, two alkyl groups, e.g., $(C_2H_5)_2NH_2^+$, three alkyl groups, e.g., $(CH_3)_3NH^+$ and four alkyl groups, e.g., $(CH_3)_4N^+$. Among the suitable thiomolybdate salts of this type utilized in the practice of the invention are (n-butylamine)$_2$H$_2$MoS$_4$, (diethylamine)$_2$H$_2$MoS$_4$, and tetra-methyl ammonium thiomolybdate, [$(CH_3)_4N]_2MoS_4$.

Among the suitable thiomolybdate salts in which the ammonium group is the cation of a cyclic amine are those in which this ammonium group contains one basic N atom, e.g., the piperidinium cation derived from piperidine and the pyrrolidinium cation derived from pyrrolidine, and those in which the ammonium group contains more than one basic N atom, e.g., the piperazinium cation derived from piperazine and the hexamethylenetetramonium cation derived from hexamethylenetetramine. Illustrative examples of amine thiomolybdates suitable for use as starting materials in the process of the invention include piperazinium thiomolybdate, $(C_4H_{10}N_2)H_2MoS_4$; piperazinium oxythiomolybdate, $(C_4H_{10}N_2)H_2MoOS_3$; hexamethylenetetramine thiomolybdate, $(C_6H_{12}N_4)_4(NH_3)_4(H_2MoS_4)_3$; piperidine thiomolybdate, $(C_5H_{11}N)_2H_2MoS_4$.

Preferred thermally decomposable thiomolybdate compounds for use in this mention are ammonium thiomolybdate of formula (I) alone in which each R group is alkyl of from 1 to 4 carbon atoms and wherein "x" is 0, and alkylated ammonium thiomolybdates, such as di-(tetramethyl ammonium) thiomolybdate, di(tetraethyl ammonium) thiomolybdate, di(tetra-n-butyl ammonium) thiomolybdate and the like.

Since mixtures of the foregoing may also be employed, it will be understood that the "x" of the total thiomolybdate compound which is employed may actually range from about 0 to about 2 within the scope of the invention.

The thiomolybdate compounds suitable as the starting materials for use in the practice of the invention are known materials that can be prepared by synthesis techniques reported in the art. These synthesis techniques do not form an essential part of the invention, which is directed to the production of improved molybdenum sulfide catalyst materials by the decomposition of known thiomolybdate compounds.

Thermal decomposition of ammonium thiomolybdate salts have been reported in the *J. Inorg. Nucl. Chemistry*, 35, 1895–1904 (1973), with the thermal decomposition of $(NH_4)_2MoO_2S_2$, $(NH_4)_2MoS_4$, $(NH_4)_2WO_2S_2$ and $(NH_4)_2 WS_4$, being disclosed, in accordance with available analytical techniques using a Mettler instrument and a DTA/TGA instrument of Linseis KG, West Germany. The experiments were carried out under nitrogen atmosphere at normal pressure employing a heating rate of 6° C./min., a heating rate of 6°–10° C./min. being conventional for such analytical procedures. At a decomposition temperature of 400° C., MoS$_2$ was reported as the probable composition. Such analytical procedures did not, however, relate to the potential advantages and disadvantages of molybdenum sulfide as an olefin oxidation catalyst.

The catalysts which are used in the process of the present invention are solids and can be employed in any suitable form, for examples as granules, pellets, powders, and the like, and they can be either used as such or supported (as is preferred) on or admixed with an inert material, such as alumina, silica, silica-alumina, zeolites, pumice, any of the activated earths, kieselguhr, clays and the like. The preferred support for the catalyst of this invention is alumina, and most preferably gamma-alumina. Preferably, the catalyst composition ranges from 1 to 30 wt. % in relation to the total weight of the supported catalyst.

The supports themselves are preferably characterized by a specific surface area of at least about 10 square meters per gram, and more preferably from about 25 to 200 square meters per gram (as determined by the BET method), and by a pore volume of at least about 0.1 cc./gm, and preferably from about 0.2 to 1.5 cc./gm (as determined by mercury porosimetry).

The molybdenum sulfide catalysts of this invention can optionally contain as a promoter a member selected from the group consisting of a metal or metal compound or complex of W, a Group VIII noble metal or a mixture thereof. Thus, also suitable as catalysts for the vapor phase process of this invention are $MoS_x$ catalysts containing, as the metal or as compounds or complexes thereof any one of W, Ru, Rh, Pd, Os, Ir and Pt. These additional elemental components of the catalyst can be present as the metals themselves (that is, in the reduced state) or as compounds or complexes thereof, or as mixtures of the foregoing. Suitable inorganic anions include oxygen, sulfur, and halogen. As with the Mo component, the W and/or noble metal will be preferably present in the form of the sulfide. Illustrative of suitable bimetallic catalysts of this invention are Rh-Mo, Pd-Mo, Os-Mo, W-Mo, Pt-Mo and Ru-Mo sulfides, and mixtures of the foregoing. Illustrative trimetallic catalysts of this invention are sulfides of Rh-Pd-Mo, Rh-W-Mo and mixtures of the foregoing.

The Mo is preferably present in the promoted catalysts of this invention in a Mo:promoter metal weight:weight ratio of from about 0.0001:1 to 10:1 and more preferably from about 0.01:1 to 1:1. Thus, Mo-Rh catalyst will preferably contain from about 0.0001 to 10 parts by weight of Mo per part by weight of Rh, and more preferably from about 0.01 to 1 part by weight of Mo per part by weight of Rh.

The promoted Mo catalysts of this invention can be prepared by impregnating the promoters onto the selected support before or after formation of the Mo sulfide catalyst, that is, before or after the thermal decomposition of the selected decomposable Mo salt.

The catalysts which are used in the process of the present invention are solids and can be employed in any suitable form, for examples as granules, pellets, powders, and the like, and they can be either used as such or supported (as is preferred) on or admixed with an inert material, such as alumina, silica, silica-alumina, zeolites, pumice, any of the activated earths, kieselguhr, clays and the like. The preferred support for the catalyst of this invention is alumina, and most preferably gamma-alumina. Most preferably, the catalyst composition ranges from 1 to 30 wt. % of catalyst metals in relation to the total weight of the supported catalyst.

The selected thiomolybdate compounds are decomposed at a decomposition temperature of from about 150° to about 600° C., preferably at a decomposition temperature of from about 200° to 500° C. The rate of heating used in the decomposition is not critical and will generally range from about 5° C./minute to about 20° C./minute, although even more rapid heating rates may be employed, as by preheating the decomposition zone to the desired preheat temperature prior to the introduction of the thiomolybdate compound into this zone.

The decomposition of the thiomolybdate compound is preferably accomplished in an essentially oxygen-free atmosphere. Thus, the decomposition can be conveniently carried out in a nitrogen or helium atmosphere or under vacuum (e.g., at a vacuum of from about 0 to −30 in Hg). Gaseous hydrogen may be present in the decomposition zone, and the hydrogen content of the gaseous volume may range from 0 to 100% by volume based on the total volume of essentially oxygen-free atmosphere in the decomposition kiln or other decomposition zone employed. Such hydrogen will ordinarily be present in amounts up to about 10% by volume of hydrogen in the overall nitrogen or argon atmosphere.

The selected thiomolybdate compound should be exposed to the decomposition conditions for sufficient time to permit decomposition of the thiomolybdate compounds. Generally, a time of from about 0.5 to 20 hours, preferably from about 1 to 3 hours, will be sufficient.

The selected thiomolybdate compound can be decomposed in bulk to form a bulk form molybdenum sulfide catalyst which can then be employed as such, or admixed with inerts, in the olefin oxidation. As is known in the art, sintering, with result on declining catalytic activity, can be retarded by mixing or matrixing the catalyst with particles of a phase which is inert. When properly compounded, the particles of the second phase serve as spacers to keep the catalyst particles separated, greatly reducing the number of contacts between catalyst particles and the opportunities for sintering or coalescence.

Alternatively, the thiomolybdate compound can be decomposed in admixture with an inert, preformed particulate diluent, e.g., a preformed, colloidal $ZrO_2$ to produce a matrixed $MoS_2$, i.e., a $MoS_2$—$ZrO_2$.

In other embodiments, the thiomolybdate compound can be bulk doped with any of the aforementioned promoters.

Preferably, however, the thiomolybdate compound is impregnated on a preformed, porous carrier such as alumina, silica, zirconia, thoria, and mixtures thereof, with such carriers being employed in a wide variety of concentrations, for example, from about 10 to about 90% by weight based on the overall weight of the thiomolybdate compound and carrier. Preferred catalyst supports are gamma-alumina and $MgAl_2O_4$.

The impregnation procedure by which the selected thiomolybdate compound is placed on the surface of the selected support, is not critical. Thus, the selected catalyst components (e.g., ammonium thiomolybdate alone or in combination with a selected promoter compound, e.g., rhodium trinitrate, are intimately mixed in the presence of a solvent so as to produce a solution or a flowable paste. Then the selected support is impregnated with this liquid mixture, as by use of vacuum impregnation, and evaporation is carried out under the selected temperature conditions to obtain a dry solids. Typically, the drying of the catalyst is conducted to remove solvent used in the impregnation and generally employs a temperature of from about 100° to 300° C., preferably from about 125° to 250° C., and in an oxygen-free atmosphere, such as a nitrogen or helium atmosphere, in vacuum or in the presence of gaseous hydrogen, as described above.

Thereafter, the support containing the impregnated thiomolybdate compound can be passed to the decomposition step, or can be again subjected to another impregnation to increase the catalyst loading. Preferably, however, the impregnated catalyst is dried after each impregnation.

The time required for drying of the solids will vary widely, and generally it will range from about 1 to 5 hours, preferably from about 1 to 3 hours at 250° C.

The solvent employed in impregnating the selected support with the thiomolybdate compound will generally be water, but oxygenated organic compounds such as alcohols, ethers, dimethyl formamide, esters, dioxane and the like can also be employed.

In the practice of the process of the invention, thermal decomposition of the thiomolybdate salt in an essentially oxygen-free atmosphere, under controlled conditions, leads to decomposition of the salt to form gaseous products, loss of some S, and of O where x in formula (I) above is greater than 0, and formulation of solid molybdenum sulfides of high surface area in what has been found to be a catalytically active form in accordance with reactions (II–IV) as follows:

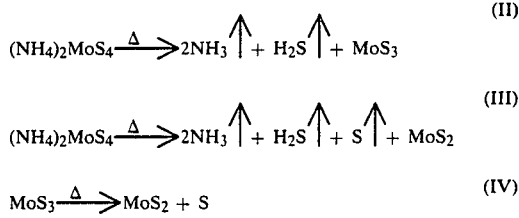

The decomposition products of the invention have the approximate composition $MoS_2$, but departures from ideal stoichiometry may occur as a result of (a) incomplete removal of sulfur during catalyst preparation, resulting in S:Mo ratios of greater than two, (b) oxidation of the catalyst surfaces when exposed to moist air, or (c) slow changes that may occur during catalytic use, such as the formation of Mo and $H_2S$ by reaction of $MoS_2$ with hydrogen, or the formation of $MoO_2$ and $H_2S$ by the reaction of $MoS_2$ with water.

Changes in stoichiometry resulting from effects (a) and (b) and falling within the S:Mo range of 1.5–2.8:1 appear to have little influence on catalytic performance. Long-term changes as a result of effect (c) are avoidable by maintaining the $H_2S:H_2$ and $H_2S:H_2O$ ratios in the reactor greater than $10^{-6}:1$ and $10^{-4}:1$, respectively. In general, it appears that, after a very short break-in period, catalytic activity appears quite insensitive to any of the indicated variations from ideal $MoS_2$ stoichiometry.

The supported catalyst thus prepared will generally have a specific surface area of at least about 5 $m^2/gm$. (and preferably at least about 40 $m^2/gm$.) and can be used in a fixed bed and can also be used in a fluidized bed or other conventional means of housing the catalyst particles for ultimate contact with the gaseous reactants.

OLEFIN CONVERSION PROCESS

The olefinic hydrocarbons which can be employed as reactants in the process of this invention are those which contain an aliphatic chain of at least two carbon atoms in which there exists at least one aliphatic double bond, —HC=CH—. Suitable olefinic hydrocarbons are those which are normally gaseous as well as those which are liquids at room temperatures but which can exist in the gaseous form at the elevated temperature and pressure conditions which are employed during the reaction. Representative olefinic reactants which can be employed, either alone or in combination, are propylene, 1-butene, 2-butene, 1-pentene, 2-pentene, 1-hexene, 2-hexene, 3-hexene, 3-methyl-1-pentene, cyclobutene, 1-heptene, 2-heptene, 1-octene, 2-octene, 1-nonene, 2-nonene, 1-decene, cyclohexene, cyclooctene, 1-dodecene, 1-hexadecene, allyl benzene, propenyl benzene, 3-phenyl-1-hexene, 4-o-tolyl-1-butene, and 1, 6-diphenyl-3-hexene. Thus, suitable olefins include (1) linear mono olefins of 2 to 20 carbon atoms, inclusive of terminal olefins, i.e., olefins, having a terminal $H_2C$=CH— group, and internal olefins having the carbon-carbon double bond, as a —HC=CH— group in an internal carbon-carbon bond of the olefin, and (2) cyclic mono-olefins of 3 to 20 carbon atoms having a —HC=CH— group in the cyclic ring. Particularly suitable for this invention are linear alkenes having from 2 to 10 carbon atoms and cycloalkenes of 4 to 10 carbon atoms, and most preferably alkenes having from 4 to 10 carbon atoms. Illustrative of these preferred classes of olefin feeds are those comprising 1-butene, 2-butene, 1-hexene, 1-pentene, propene, 1-octene, cyclohexene, cyclopentene, cyclobutene and the like, and mixtures thereof.

Paraffins (such as alkanes of 2 to 20 carbon atoms) and isoolefins (i.e., olefins having a >C=C< group in which one or both carbon atoms are hydrocarbyl substituted, such as 2-methyl-2-butene) can be also present in the gas feed to the reaction zone in the practice of this invention, but they are essentially unreactive in forming the desired ketones.

Preferred olefinic feeds are olefin gas mixtures obtained from the refining of crude oil. Thus, butene cuts from such refineries typically contain n-butenes (1-butene and 2-butene) which will be converted by this process into 2-butanone, and also typically contain butane and isobutene.

The process of this invention is effected by passing the selected olefin, water vapor and $O_2$ (if employed) over the surface of a catalyst of this invention under conditions such as to maintain a vaporous olefin in the reaction zone. The conditions of temperature and pressure under which this can be performed can vary widely depending on such factors as the particular olefin selected for use, the space velocity of gases through the reactor and other factors. Generally, however, a temperature of from about 125° to 600° C., preferably from about 200° to 400° C., will be entirely suitable. Most preferably, where the alkene comprises butene-1 or butene-2, the temperature within the catalyst reactor is maintained within the range of from about 250° to 375° C. Similarly, for cycloalkenes such as cyclohexene, a temperature in the range of from about 125° to about 200° C. is most preferable. The pressures are in no way critical and will generally range from about 0 to 2000 psig, preferably from about 5 to 150 psig, although higher or lower pressures are also suitable.

The space velocity of the total gases through the oxidation reactor are also not critical and can range from 100 to 10,000 v/v/hr., and preferably from about 200 to 6,000 v/v/hr., where "v" represents a unit of volume (e.g., "cc").

Preferably, the olefin, water vapor and $O_2$ (if employed) are contacted with a catalyst of this invention in the substantial absence of free halide (that is a molar ratio of free halide:olefin of less than about $1 \times 10^{-5}:1$) in order to minimize corrosion difficulties.

Also, the process of this invention is preferably conducted in the substantial absence of added $H_2S$, that is in a molar ratio of added $H_2S$:olefin of less than about 0.01:1. Hydrogen sulfide is not a required feed component, thereby avoiding the purification expense associated with prior art processes in which $H_2S$ is fed to the reaction zone.

The reaction can be carried out either batchwise, continuously, or semi-continuously. In batch operation, the gaseous reactants may be placed, together with the catalyst, in a suitable pressure vessel and allowed to remain there under the desired reaction conditions for a suitable reaction interval, which will generally range from about 0.01 to 10 hours or more, depending on the degree of reaction completeness sought. In continuous operation, the gaseous reactants are passed through a body of the catalyst supported within a reactor vessel, which can be any of the conventional equipment employed by the industry for such reactions.

The water vapor (and $O_2$, when employed) can be combined and premixed with, or introduced separately from, the olefin feed, or they can be passed to the reaction vessel via separate conduits. The manner of contacting the water vapor and olefin is not critical and any of the conventional gas-gas contacting methods employed in the industry may be used.

The ratio of olefin:water vapor can also vary widely. Generally, the molar ratio of olefin:water vapor introduced to the reactor will range from about 2:1 to 1:20, preferably from about 1:1 to 1:10. When $O_2$ is employed, the molar ratio of olefin:oxygen in the total gases fed to the reactor will generally range from about 0.5:1 to 10:1, and more typically from about 1:1 to 5:1. However, ratios outside the foregoing ranges can also be employed.

An inert gaseous diluent such as nitrogen or paraffin can also be introduced together with the other gaseous feeds to the reactor in order to achieve a desired high space velocity and to minimize hot spots which could result in an over-oxidation of the feed and/or reactants during the exothermic ketone formation using an $O_2$-containing feed.

The ketones which are formed will depend, of course, on the particular olefin(s) employed in the feed. Thus, use of alkene as the olefin will result in forming the corresponding alkanone having the same number of carbon atoms as the alkene fed (acetone from propylene; methyl ethyl ketone from 1-butene, 2-butene or mixtures thereof; cyclohexanone from cyclohexene). The process is particularly suitable for forming alkanones having from 4 to 10 carbon atoms.

The major alcohol product formed in the process of this invention will correspond to the carbon skeleton of the ketone product, e.g., secondary butyl alcohol corresponding to methyl ethyl ketone.

The reaction zone, in which the desired reaction between the olefin and water vapor to form the selected ketone is effected, is preferably oxygen-free, that is, contains a molar ratio of added molecular oxygen to olefin of less than about 0.01:1. Molecular oxygen, therefore, is not a preferred component of the gas feed to the process and its presence serves to increase the amount of oxygenated by-products, including carbon dioxide and carbon monoxide, as will be illustrated in the examples which follow.

The ketones and alcohols produced by the process of this invention can be recovered from the reaction mixture in any desired manner, such as by distillation or by extraction with water or other solvents followed by distillation. Preferably, at least a portion of the unreacted gases are recovered and recycled to the reactor in addition to fresh feed gases in order to maximize olefin conversion. Alternatively, a series of reactor vessels can be employed and the unreacted gases from the first vessel can then be passed as feed to the second vessel, together with make-up gaseous olefin and water vapor as required.

The choice of whether or not to employ molecular oxygen in the gas feed to the reaction zone may be made based on a variety of process parameters. An oxygen-containing gas feed will yield a more exothermic reaction and hence will provide an opportunity for higher level heat recovery from the reaction effluent. On the other hand, use of oxygen in the feed generally results in an increase in the amount of by-products which are made, such as CO and $CO_2$, although this is balanced by an increase in olefin conversions over comparative reactions in which molecular oxygen is excluded from the reaction zone. Of course, the precise balance of these potential benefits and disadvantages of oxygen-containing feeds must be made on a case-by-case basis.

While not wishing to be limited thereby, it is believed that the ketone product formed by the partial oxidation process of this invention proceeds by way of an alcohol intermediate corresponding to the skeleton structure of the ketone product. It is believed that this is the explanation for the quantity of alcohol product which is also formed and detected in the examples that follow. For example, butene is oxidized to a mixture of ketone and secondary butyl alcohol. Accordingly, our invention also provides a process for contacting such an alcohol with water vapor in the presence of a catalyst of this invention to form a corresponding ketone. Optionally, $O_2$ can also be employed in the gaseous feed. Process parameters including feed ratios, reaction times, space velocities, temperatures, pressures and the like which are discussed above for the olefin partial oxidation process, are also useful in the embodiment of this invention in which the alcohol is employed as the feed. The molar ratio of alcohol:water vapor is generally from about 0.01:1 to 100:1, and preferably from about 0.1:1 to 10:1. When $O_2$ is employed, the alcohol:oxygen molar ratio will generally be from about 0.1:1 to 100:1, preferably 1:1 to 10:1. Alcohols which are suitable as feeds correspond to any of the above-discussed product alcohols of this invention. Therefore, particularly suitable are alklanols, and especially secondary alkanols, having from 3 to 10 carbon atoms per molecule. The utility of the catalysts of this invention for conversion of alcohols to ketones can be readily seen from the following examples, and it will also be apparent to one skilled in the art that recycle of recovered alcohol by-product to an olefin-reaction zone using a catalyst of this invention will provide improved overall utilization of an olefin-containing feed as a result of the further reaction of the thus-recycled alcohol by-product.

The process of this invention can be further illustrated by reference to the following examples wherein % conversions and selectivities are mole %.

Product selectivities in the examples were determined by gas chromatographic (GC) analysis after steady-state conditions were observed. Products formed were methyl ethyl ketone, CO, $CO_2$, secondary butyl alcohol, butyl mercaptan and the balance unknowns. In the Examples, the gaseous effluents from the reactor were analyzed for butene consumed, using isobutane as a standard and employing response factors determined for the GC by calibration with a known gas mixture.

EXAMPLE 1

Thirty cc. of gamma-alumina (12–20 mesh; 100 $m^2/gm$ surface area; 0.45 cc./gram pore volume; Alfa Products) were dried in a Linberg furnace at 250° C. in air for 2.3 hours to a dry weight of 26.6 grams. A calculated amount of ammonium tetrathiomolybdate (6.85 grams $(NH_4)_2MoS_4$) was dissolved in 61 cc. of distilled water and 11 cc. of the solution was transferred into a 60 cc. dropping funnel. The catalyst support was put in a glass filtering flask (125 ml) equipped with a sidearm for pulling a vacuum and the dropping funnel was attached using a rubber stopper. After evacuation of the air in the flask (to a pressure of −15 in Hg) the ammonium tetrathiomolybdate solution was added dropwise to the catalyst support to achieve complete wetness. The impregnated wet catalyst was placed in a stainless steel gauze boat and dried in a Linberg furnace under helium (4 psig) at 125° C. for 1 hour and 250° C. for 1 hour. Then, the solids were allowed to cool to room temperature. The impregnation and drying procedure was then repeated five times in the above solution using 10 cc. each, for a total of six successive impregnations to use up the 61 cc. of solution.

After the last impregnation and drying, the dried solids, rather than being allowed to cool to room temperature, were calcined by raising the furnace temperature (at a rate of about 10° C./min.) to 350° C., which was maintained for 3 hours. After this time, the catalyst was allowed to cool to room temperature in the inert atmosphere and was found to comprise $MoS_2$ on gamma-alumina, with a catalyst loading of 7.5 wt. %, calculated as elemental Mo on the basis of catalyst support.

Ten cc. of the thus-prepared supported catalyst was well mixed with 20 cc. of inert solids (12–20 mesh fused ceramic) and was loaded to a 24 inch (0.38 in. I.D.) tubular reactor equipped with a gas inlet at one end and a gas outlet to the other. The reactor was then heated to a temperature of 300° C. Temperature control of the reactor was maintained by use of an electric heating tape and a Gardsman temperature control. Temperatures in the reactor were determined by use of a thermocouple positioned at the center of the catalyst bed.

A gas feed containing the selected mix of butene-1, $N_2$ and water vapor was then passed to the lower end of the reactor at the selected feed rate. Exiting gases were analyzed by means of an on-line gas chromatograph. A series of runs were made using selected temperatures, pressures and flow rates. Run 1 was conducted for a time of 4.5 hours, at which time the gas products' analysis was determined (see Table I). The catalyst used in Run 1 was again used in Run 2 at a slightly higher temperature and at a lower gas hourly space velocity. At the end of Run 2 (6.5 hours), the catalyst was contacted in the reactor at a temperature of 325° C. and a gas inlet pressure of 63 kpa with $H_2S$, passed over the catalyst as a mixture of $H_2S$ (190 cc./min.; fed as 6 vol. % $H_2S$ in $N_2$) and $H_2$ (230 cc./min.) for one hour to determine the effect of additional sulfiding on the catalyst. (After this one hour of $H_2S$ treatment, gaseous $H_2$ feed was continued for one hour, at a rate of 520 cc./min., and at 325° C., to strip any excess $H_2S$ from the reactor to avoid product contamination with the $H_2S$ which would complicate the product analysis.) Then, the thus-treated catalyst was employed in Run 3, which employed an $O_2$-containing gas feed. The data thereby obtained is set forth in Table I below.

TABLE I

| Run No. | Time (hrs) | Temp. (°C.) | Press. kpa | Gas Feed (cc/min.) Butene (1) | $H_2O$ Vapor | $N_2$ (2) | $O_2$ (3) | GHSV (cc/cc hr.) (4) | Butene Conv. (%) | % Selectivities to: MEK (5) | $CO_2$ | CO | SBA (6) | $C_4SH$ (7) | Other (8) |
|---|---|---|---|---|---|---|---|---|---|---|---|---|---|---|---|
| 1 | 4.5 | 298 | 64 | 102 | 224 | 730 | 0 | 6336 | 5.9 | 94.9 | 0 | 0 | 3.3 | 1.8 | nil |
| 2 | 6.5 | 299 | 64 | 60 | 224 | 380 | 0 | 3984 | — | 95.2 | 0 | 0 | 3.3 | 1.5 | nil |
| 3 | 2.0 | 303 | 64 | 60 | 224 | 0 | 380 | 3984 | 4.0 | 87.3 | 0 | 0 | 5.1 | 3.8 | 3.8 |

(1) Feed = 85 vol. % butene-1, 15 vol. % n-butane.
(2) Fed as pure $N_2$.
(3) Fed as a 10 vol. % $O_2$, 90 vol. % $N_2$ mixture.
(4) Gas hourly space velocity.
(5) Methyl ethyl ketone.
(6) Secondary butyl alcohol.
(7) Butyl mercaptan.
(8) Unknowns.

EXAMPLE 2

Thirteen cubic centimeters of gamma-alumina (12–20 mesh; Alfa Products) were dried in a Linberg furnace at 500° C. in air for 3 hours, giving a dry weight of 11.03 grams. Ammonium tetrathiomolybdate (2.23 grams) was then dissolved in 25 cc. of distilled water, and 0.152 grams of a concentrated (30% $NH_3$) ammonium hydroxide solution was added in order to enhance the solubility of the Mo salt. Thereafter, excess ammonium hydroxide was neutralized by adding 0.538 grams of glacial acetic acid to the thiomolybdate solution, and the neutralized solution was employed to vacuum impregnate the dried gamma-alumina in five successive impregnations employing the vacuum impregnation and drying procedures described in Example 1. After the fifth impregnation, the temperature in the furnace was raised at a rate of 10° C./min. to 350° C., which was then maintained for 3 hours to decompose the thiomolybdate supported on the gamma-alumina and to form an alumina having molybdenum sulfide thereon. The supported catalyst was found to have a catalyst loading of 7.5 wt. % Mo, calculated as elemental molybdenum on the basis of catalyst support.

After permitting the catalyst to cool to room temperature, 10 cc. of the molybdenum sulfide catalyst was mixed with 20 cc. of inert solids (12–20 mesh fused ceramic) and was then employed in a butene oxidation using the procedure of Example 1. The reaction was carried out for a period of about 28 hours at the conditions indicated in Table II below, without noticeable loss of catalyst activity. The data thereby obtained for Runs 1 through 7 are set forth in Table II. After 28 hours of operation, the gas feed to the catalyst bed was replaced with hydrogen sulfide gas which was charged at a reactor temperature of 325° C. and a pressure of 65 kpa of a 6 vol. % $H_2S$ mixture in nitrogen with 190 cc./min. together with 230 cc./min. of gaseous hydrogen for 1 hour at a total gas flow rate of 420 cc./min. Thereafter, the gas feed was changed to hydrogen gas to remove any adsorbed, unreacted $H_2S$. The hydrogen feed rate for the stripping step was 520 cc./min., which was continued for a time of 1 hour at the same temperature and pressure. Thereafter, feed of the selected butene-containing gas was resumed under the conditions of temperature and pressure noted for Runs 1 through 2 in Table III and again no noticeable change in catalyst activity was observed over a period of 4.0 hours (2.5 hours Run 1; 4.0 hours, Run 2). This is another indication that there was no significant loss of sulfur from the catalyst during the first 28 hours of operation, an observation which is confirmed by the very low levels detected for sulfur-containing by-products, as shown in Table III.

EXAMPLE 3

One-eighth inch diameter pellets of gamma-alumina (100 $m^2$/gm; 0.45 cc./gm. pore volume; Alfa Products) were crushed to 12–20 mesh and dried as in Example 1 in air at 250° C. for 3 hours to a dry weight of 12.7 grams. Fifteen cc. of these dried solids were then impregnated in six successive impregnations using the procedure of Example 1. The solution employed to impregnate the solids was prepared by dissolving 2.592 grams of ammonium tetrathiomolybdate in 30 cc. of distilled water to which was added 0.599 grams of concentrated ammonium hydroxide (30% $NH_3$). Following stirring of this ammonium tetrathiomolybdate solution for one-half hour using a magnetic stirrer, 0.613 grams of glacial acetic acid was added to neutralize the excess ammonium hydroxide present. After each impregnation, the impregnated catalyst solids were dried at 125° C. for 1 hour and 250° C. for 1 hour, each in helium. After the final impregnation, the temperature in the furnace was raised (at a rate of 6° C./min.) to 350° C., which was maintained for 3 hours, for thermal decomposition of the thiomolybdate compound to molybdenum sulfides. The catalyst thereby obtained was found to comprise 7.5 wt. % molybdenum, based on the total weight of the catalyst support.

Ten cc. of this molybdenum sulfides catalyst was mixed with 20 cc. of fused ceramic inerts of 12 to 20 mesh and this mixture was then loaded into the reactor and tested as in Example 1. The reaction conditions and data thereby obtained are set forth in Table IV.

TABLE II

| Run No. | Time (hrs) | Temp. (°C.) | Press. kpa | Gas Feed (cc/min.) Butene (1) | $H_2O$ Vapor | $O_2$ (2) | GHSV (cc/cc hr.) (3) | Butene Conv. (%) | % Selectivities to: MEK (5) | $CO_2$ | CO | SBA | $C_4SH$ | Others (4) |
|---|---|---|---|---|---|---|---|---|---|---|---|---|---|---|
| 1 | 6.3 | 299 | 64 | 102 | 224 | 730 | 6336 | 3.4 | 90.7 | 0 | 0 | 7.1 | 1.0 | 1.2 |
| 2 | 10.5 | 285 | 63 | 60 | 224 | 730 | 6084 | — | 76.3 | 0 | 0 | 23.7 | 0 | 0 |
| 3 | 19.0 | 310 | 64 | 102 | 224 | 730 | 6336 | — | 89.1 | 0 | 0 | 8.5 | 1.0 | 2.4 |
| 4 | 20.0 | 307 | 64 | 102 | 224 | 730 | 6336 | 3.3 | 88.7 | 0 | 0 | 10.7 | 1.0 | 0.6 |
| 5 | 21.5 | 307 | 65 | 102 | 224 | 730 | 6336 | 3.6 | 93.4 | 0 | 0 | 1.8 | 1.0 | 4.8 |
| 6 | 27.5 | 310 | 65 | 102 | 224 | 730 | 6336 | 3.4 | 89.8 | 0 | 0 | 9.0 | 1.0 | 1.2 |
| 7 | 28.0 | 308 | 65 | 102 | 224 | 730 | 6336 | 3.4 | 90.7 | 0 | 0 | 8.3 | 1.0 | 1.0 |

(1) Feed = 85 vol. % butene-1, 15 vol. % n-butane.
(2) Fed as a 10% $O_2$, 90% $N_2$ mixture.
(3) Gas hourly space velocity.
(4) Unknowns.

TABLE III

| Run No. | Time (hrs) | Temp. (°C.) | Press. kpa | Gas Feed (cc/min.) Butene (1) | $H_2O$ Vapor | $O_2$ (2) | GHSV (cc/cc hr.) (3) | Butene Conv. (%) | % Selectivities to: MEK | $CO_2$ | CO | SBA | $C_4SH$ | Others (4) |
|---|---|---|---|---|---|---|---|---|---|---|---|---|---|---|
| 1 | 2.5 | 305 | 63 | 102 | 224 | 730 | 6336 | 3.0 | 92.5 | 0 | 0 | 4.5 | 2.1 | 0.9 |
| 2 | 4.0 | 302 | 64 | 60 | 224 | 380 | 3984 | — | 83.8 | 0 | 0 | 14.4 | 0.7 | 1.1 |

(1) Feed = 85 vol. % butene-1, 15 vol. % n-butane.
(2) Fed as a 10% $O_2$, 90% $N_2$ mixture.
(3) Gas hourly space velocity.
(4) Unknowns. All other terms as defined for Table I.

TABLE IV

| Run No. | Time (hrs) | Temp. (°C.) | Press. kpa | Gas Feed (cc/min.) Butene (1) | $H_2O$ Vapor | $O_2$ (2) | GHSV (cc/cc hr.) (3) | Butene Conv. (%) | % Selectivities to: MEK | $CO_2$ | CO | SBA | $C_4SH$ | Others (4) |
|---|---|---|---|---|---|---|---|---|---|---|---|---|---|---|
| 1 | 1.8 | 307 | 66 | 102 | 224 | 730 | 6336 | 9.4 | 70.9 | 1.9 | 1.9 | 13.3 | 3.0 | 9.0 |
| 2 | 2.2 | 307 | 67 | 102 | 224 | 730 | 6336 | 7.3 | 69.0 | 2.2 | 2.2 | 16.6 | 1.2 | 8.8 |

TABLE IV-continued

| Run No. | Time (hrs) | Temp. (°C.) | Press. kpa | Gas Feed (cc/min.) Butene (1) | Gas Feed (cc/min.) $H_2O$ Vapor | Gas Feed (cc/min.) $O_2$ (2) | GHSV (cc/cc hr.) (3) | Butene Conv. (%) | % Selectivities to: MEK | % Selectivities to: $CO_2$ | % Selectivities to: CO | % Selectivities to: SBA | % Selectivities to: $C_4SH$ | Others (4) |
|---|---|---|---|---|---|---|---|---|---|---|---|---|---|---|
| 3 | 3.4 | 255 | 67 | 102 | 224 | 730 | 6336 | 1.8 | 73.7 | 0 | 0 | 24.5 | 0 | 1.8 |

(1) Feed = 85 vol. % butene-1, 15 vol. % n-butane.
(2) Fed as a 10% $O_2$, 90% $N_2$ mixture.
(3) Gas hourly space velocity.
(4) Unknowns. All other terms as defined for Table I.

EXAMPLE 4 FOR COMPARISON

To illustrate the advantages achieved by use of the molybdenum sulfide catalyst of this invention prepared by thermal decomposition of thiomolybdate salts, a series of runs were conducted employing molybdenum sulfides prepared by calcining of ammonium paramolybdate, $(NH_4)_6Mo_7O_{24}.4H_2O$ and sulfiding the resulting oxides. Following the procedure of Example 1, 45 cc. of the same gamma-alumina used in that Example was dried in air at 250° C. for 2 hours to provide a dry weight of 37.1 grams. Thereafter, 6.5 grams of ammonium paramolybdate was dissolved in distilled water to make a 18.0 cc. solution. The resulting solution was employed in vacuum impregnation of the dried gamma-alumina solids using the procedure of Example 1. After the vacuum impregnation, the wet solids were dried in air at a temperature of 125° C. for 1 hour and a temperature of 250° C. for 1 hour, followed by 350° C. for 1 hour, and then calcined in nitrogen at 500° C. for 3 hours. The catalyst was found to comprise molybdenum oxides on gamma-alumina, which could be represented by the formula: $MoO_3$. The catalyst loading was found to be 9.5% of molybdenum, calculated as the element, based on the total weight of the catalyst support.

Ten cc. of the supported catalyst was then charged to the reactor after mixing the catalyst with 20 cc. of fused ceramic inert (12–20 mesh). This oxide catalyst was then employed in two runs (Runs 1 and 2) under the conditions of temperature and feed rates summarized in Table V, yielding the data set forth in that Table.

Thereafter, the oxide catalyst was subjected to an in situ sulfiding procedure in which the butene-gas feed was replaced by a hydrogen sulfide gas feed comprising a mixture of (1) a gas containing 6 vol. % $H_2S$ in nitrogen (190 cc./min.) and (2) gaseous hydrogen (230 cc./min.) to provide a total gas feed rate during the in situ sulfiding of 420 cc./min., at a gas inlet pressure of about 7.1 psig. The catalyst temperature during the sulfiding was maintained at 325° C., and the sulfiding was carried out for 3 hours, to convert the catalyst to the molybdenum sulfide form. After 3 hours, the gas feed composition was altered to pass pure hydrogen over the catalyst solids at a rate of 520 cc./min., at 325° C. for 1 hour to remove any excess unreacted $H_2S$. Thereafter, the butene-gas feed was resumed in a series of runs at the indicated conditions, thereby obtaining the data set forth in Table V, for Runs 3 and 4.

These data show that Mo sulfide catalysts prepared by sulfiding of molybdenum oxide provide greatly inferior selectivities to ketone and alcohol products, as compared to the catalysts of this invention which are prepared from certain thermally decomposable compounds. Thus, overall (MEK+SBA) product selectivities for Runs 3 and 4 of this comparative example ranged from only 76.2 to 78.4%, and the total carbon oxides selectivity loss ($CO_2$+CO) ranged from 7.7 to 12%. In contrast, in the runs of Examples 1–3, which also employed $O_2$-containing feeds in a similar amount of catalyst solids, overall product selectivities (MEK+SBA) of from 84 to 100% were observed, and $CO_2$+CO by-product selectivities ranged from 0 to only 4.4%.

TABLE V

| Run No. | Time (hrs) | Temp. (°C.) | Press. kpa | Gas Feed (cc/min.) Butene (1) | Gas Feed (cc/min.) $H_2O$ Vapor | Gas Feed (cc/min.) $O_2$ (2) | GHSV (cc/cc hrs) (3) | Butene Conv. (%) | % Selectivities to: MEK | % Selectivities to: $CO_2$ | % Selectivities to: CO | % Selectivities to: SBA | % Selectivities to: $C_4SH$ | Others (4) |
|---|---|---|---|---|---|---|---|---|---|---|---|---|---|---|
| 1 | 2.0 | 300 | 50 | 60 | 224 | 730 | 6084 | 9.1 | 80.6 | 6.9 | 2.8 | 8.1 | 0 | 1.6 |
| 2 | 5.0 | 305 | 50 | 102 | 224 | 730 | 6338 | 20.4 | 71.0 | 3.8 | 1.9 | 4.2 | 0 | 19.1 |
| 3 | 5.2 | 305 | 50 | 60 | 224 | 730 | 6084 | 15.1 | 62.6 | 10.0 | 2.0 | 13.6 | 0.9 | 22.9 |
| 4 | 6.0 | 298 | 50 | 102 | 224 | 730 | 6338 | 12.6 | 68.8 | 5.8 | 1.9 | 9.6 | 0.9 | 13.0 |

(1) Feed = 85 vol. % butene-1, 15 vol. % n-butane.
(2) Fed as a 10% $O_2$, 90% $N_2$ mixture.
(3) Gas hourly space velocity.
(4) Unknowns. All other terms as defined for Table I.

EXAMPLE 5

Following the procedure of Example 1, 45 cc. of gamma-alumina (16–25 mesh; 100 $m^2$/gm; 0.45 cc.gm pore volume; Alfa Products) was dried at 500° C. in air for 3 hours to a dry weight of 38.7 grams. In this preparation, 7.84 grams of ammonium tetrathiomolybdate was divided into eight equal portions, and each portion of the thiomolybdate solids was dissolved in 14 cc. of distilled water. Each such thiomolybdate solution was then employed for a vacuum impregnation of the dried gamma-alumina support following the procedure of Example 1. After each impregnation, the wet solids were dried at 125° C. in helium for one-half hour, followed by drying at 250° C. in helium for another one-half hour. Thus, the solids were subjected to eight separate vacuum impregnation and drying steps. At the end of the last drying step, the temperature in the furnace was raised to 350° C. at a rate of 10° C. per minute and the 350° C. temperature was maintained for 3 hours to thermally decompose the thiomolybdate to molybdenum sulfide. The thus-obtained supported molybdenum sulfide catalyst was found to contain 6.84 wt. % molybdenum (calculated as elemental molybdenum), based on the total weight of the catalyst support.

Then, 30 cc. of the thus-prepared supported catalyst (30.44 grams) was loaded into the reactor and contacted with the selected feed using the procedure of Example 1, except that no inerts (fused ceramic) were employed. In the first run, a butene-containing gas which also contained oxygen, was passed to the reactor under the selected conditions of temperature and pressure to determine the effect of absence of the fused ceramic inerts. The data thereby obtained are set forth in Table VI.

Then, the feed to the reactor was altered to substitute pure nitrogen for the oxygen:nitrogen gas mixture to pass a butene-containing gas which was substantially oxygen-free over the catalyst. The conditions of temperature, pressure and gas flow rates were varied, and the data thereby obtained are set forth also in Table VI.

TABLE VI

| Run No. | Time (hrs) | Temp. (°C.) | Press. kpa | Gas Feed (cc/min.) Butene (1) | Gas Feed (cc/min.) H$_2$O Vapor | Gas Feed (cc/min.) N$_2$ (2) | Gas Feed (cc/min.) O$_2$ (3) | GHSV (cc/cc hr.) (4) | Butene Conv. (%) | % Selectivities to: MEK | % Selectivities to: CO$_2$ | % Selectivities to: CO | % Selectivities to: SBA | % Selectivities to: C$_4$SH | Other (%) |
|---|---|---|---|---|---|---|---|---|---|---|---|---|---|---|---|
| 1 | 0.7 | 299 | 65 | 60 | 224 | 0 | 380 | 1328 | 13.1 | 40.1 | 17.9 | 10.7 | 2.5 | 11.4 | 28.8 |
| 2 | 3.4 | 293 | 66 | 60 | 224 | 380 | 0 | 2112 | 0.9 | 88.7 | 0 | 0 | 11.3 | 0 | 0 |
| 3 | 4.5 | 306 | 66 | 102 | 224 | 730 | 0 | 1328 | 2.5 | 93.1 | 0 | 0 | 6.9 | 0 | 0 |
| 4 | 5.5 | 372 | 66 | 102 | 224 | 730 | 0 | 2112 | 4.5 | 90.8 | 0 | 0 | 2.4 | 0 | 6.8 |
| 5 | 6.5 | 382 | 66 | 60 | 224 | 380 | 0 | 1328 | 2.0 | 90.9 | 0 | 0 | 2.9 | 1.0 | 6.2 |

(1) Feed = mixture containing 85 vol. % butene-1, 15 vol. % n-butane.
(2) Fed as pure N$_2$.
(3) Fed as a 10 vol. % O$_2$, 90 vol. % N$_2$ mixture.
(4) Gas hourly space velocity.
(5) Unknowns. All other terms as defined for Table I.

In each of the foregoing examples illustrative of the process of this invention, butane by-product was observed to be formed from the butene feeds in selectivities of less than about 0.5 mol. %, based on the butene fed to the reactor. Thus, the improved process of this invention allows the formation of the desired ketone in the substantial absence of olefin hydrogenation by-products, that is, the hydrogenation by-products will be generally formed in a selectivity of less than about 1 mol. %, based on the olefin fed.

Preferably, monoolefin feeds to the process of this invention are substantially free (e.g., contain less than 1 wt. %) of diolefins or acetylenic hydrocarbons to obtain the highest catalyst activity to form the ketones corresponding to the monoolefin feeds.

It will be obvious that various changes and modifications may be made without departing from the invention and it is intended, therefore, that all matter contained in the foregoing description shall be interpreted as illustrative only and not limitative of the invention.

What is claimed is:

1. An improved process for preparing ketones which comprises contacting an olefin in the gaseous phase in the substantial absence of free molecular oxygen in the presence of water vapor and in the additional presence of a molybdenum sulfides catalyst, prepared by the thermal decomposition of a thiomolybdate compound, under conditions sufficient to form the corresponding ketone from said olefin, said olefin comprising a member selected from the group consisting of linear monoolefins of from 2 to 20 carbon atoms and cyclic monoolefins of from 3 to 20 carbon atoms, said thiomolybdate compound comprising at least one member selected from the group consisting of ammonium salts of molybdenum-sulfur cluster anions and compounds of the formula:

$$[R^1(R^2)N(R^3)R^4]_2MoO_xS_{4-x}$$

wherein $R^1$, $R^2$, $R^3$ and $R^4$ can be the same or different and are hydrogen, alkyl, aryl, alkaryl, aralkyl, cycloalkyl, substituted derivatives of the above groups and mixtures thereof, and x is 0, 1 or 2, and said thermal decomposition being conducted at a temperature of from about 150° to 600° C.

2. The process according to claim 1 wherein said thiomolybdate compound is selected from the group consisting of ammonium thiomolybdate, ammonium oxo thiomolybdate, and alkylated ammonium thiomolybdates.

3. The process according to claim 1 wherein said molybdenum sulfides catalyst is characterized by a specific surface area of at least about 5 square meters per gram.

4. The process according to claim 1 wherein said molybdenum sulfides compound is supported on an inert support.

5. The process according to claim 4 wherein said supported molybdenum sulfides catalyst is prepared by impregnating said thiomolybdate salt on said inert support and thermally decomposing said supported thiomolybdate compound at a temperature within the range of from about 200° to 500° C. and in an oxygen-free atmosphere.

6. The process according to claim 5 wherein said inert support comprises gamma-alumina.

7. The process according to claim 1 wherein said olefin comprises an alkene having from 4 to 10 carbon atoms.

8. The process according to claim 1 wherein said olefin comprises butene, said molybdenum sulfides catalyst is supported on gamma-alumina and said process is effected by contacting butene and water vapor in the presence of said molybdenum sulfides catalyst at a temperature of from about 200° to 400° C. and at a pressure of from about 5 to 150 psig to form methyl ethyl ketone.

9. The process according to claim 1 wherein said catalyst additionally comprises at least one promoter selected from the group consisting of a compound or complex of W and a Group VIII noble metal.

10. An improved process for preparing ketones which comprises contacting an olefin in the gaseous phase, in the substantial absence of H$_2$S, in the presence of water vapor and molecular oxygen and in the additional presence of a molybdenum sulfides catalyst, prepared by the thermal decomposition of a thiomolybdate compound, under conditions sufficient to form the corresponding ketone from said olefin, said olefin comprising a member selected from the group consisting of linear mono-olefins of from 2 to 20 carbon atoms and cyclic monoolefins of from 3 to 20 carbon atoms, said thiomolybdate compound comprising at least one member selected from the group consisting of ammonium salts of molybdenum-sulfur cluster anions and compounds of the formula:

$$[R^1(R^2)N(R^3)R^4]_2MoO_xS_{4-x}$$

wherein $R^1$, $R^2$, $R^3$ and $R^4$ can be the same or different and are hydrogen, alkyl, aryl, alkaryl, aralkyl, cycloalkyl, substituted derivatives of the above groups and mixtures thereof, and x is 0, 1 or 2, and said thermal decomposition being conducted at a temperature of from about 150° to 600° C.

11. The process according to claim 10 wherein said thiomolybdate compound is selected from the group consisting of ammonium thiomolybdate, ammonium oxo thiomolybdate, and alkylated ammonium thiomolybdates.

12. The process according to claim 10 wherein said molybdenum sulfides catalyst is characterized by a specific surface area of at least about 5 square meters per gram.

13. The process according to claim 10 wherein said molybdenum sulfides compound is supported on an inert support.

14. The process according to claim 13 wherein said supported molybdenum sulfides catalyst is prepared by impregnating said thiomolybdate salt on said inert support and thermally decomposing said supported thiomolybdate compound at a temperature within the range of from about 200° to 500° C. and in an oxygen-free atmosphere.

15. The process according to claim 14 wherein said inert support comprises gamma-alumina.

16. The process according to claim 10 wherein said olefin comprises an alkene having from 4 to 10 carbon atoms.

17. The process according to claim 10 wherein said olefin comprises butene, said molybdenum sulfides catalyst is supported on gamma-alumina and said olefin oxidation process is effected by contacting butene and water vapor in the presence of said molybdenum sulfides catalyst at a temperature of from about 200° to 400° C. and at a pressure of from about 5 to 150 psig to form methyl ethyl ketone.

18. The process according to claim 10 wherein said catalyst additionally comprises at least one promoter selected from the group consisting of a compound or complex of W and a Group VIII noble metal.

19. The process according to claim 1 wherein said olefin, water vapor and catalyst are contacted in a reaction zone employing a space velocity of total gases through the reaction zone of from 100 to 10,000 cc/cc/hr.

20. The process according to claim 10 wherein said olefin, water vapor and catalyst are contacted in a reaction zone employing a space velocity of total gases through the reaction zone of from 100 to 10,000 cc/cc/hr.

* * * * *